United States Patent [19]
Chalifoux

[11] Patent Number: 5,437,551
[45] Date of Patent: Aug. 1, 1995

[54] DENTAL IMPLANT POST AND PROSTHESIS CONSTRUCTION

[75] Inventor: Paul R. Chalifoux, Wellesley, Mass.

[73] Assignee: Wellesley Research Associates, Inc., Wellesley, Mass.

[21] Appl. No.: 75,809

[22] Filed: Jun. 14, 1993

Related U.S. Application Data

[63] Continuation-in-part of Ser. No. 896,602, Jun. 10, 1992, Pat. No. 5,312,253, which is a continuation-in-part of Ser. No. 814,507, Dec. 30, 1991, Pat. No. 5,197,881.

[51] Int. Cl.⁶ .............................................. A61C 8/00
[52] U.S. Cl. .................................... 433/173; 433/172
[58] Field of Search ............... 433/172, 173, 174, 175, 433/176

[56] References Cited

U.S. PATENT DOCUMENTS

| | | | |
|---|---|---|---|
| 4,575,340 | 3/1986 | Lustig | 433/173 |
| 4,780,080 | 10/1988 | Haris | 433/173 |
| 5,195,892 | 3/1993 | Gersberg | 433/173 |

FOREIGN PATENT DOCUMENTS 9309728  5/1993  WIPO ................... 433/173

Primary Examiner—Cary E. O'Connor
Attorney, Agent, or Firm—Paul J. Cook

[57] ABSTRACT

A dental implant is provided for insertion into the jawbone of a patient for the purpose of building a dental prosthesis thereon. The implant includes a central hole having a wall with first extension for accommodating a dental post having a second extension that frictionally interlock with the first extension. A core can be provided which includes a second central hole having a wall with a third extension for accommodating a dental post having a fourth extension that frictionally interlocks with the third extension.

26 Claims, 15 Drawing Sheets

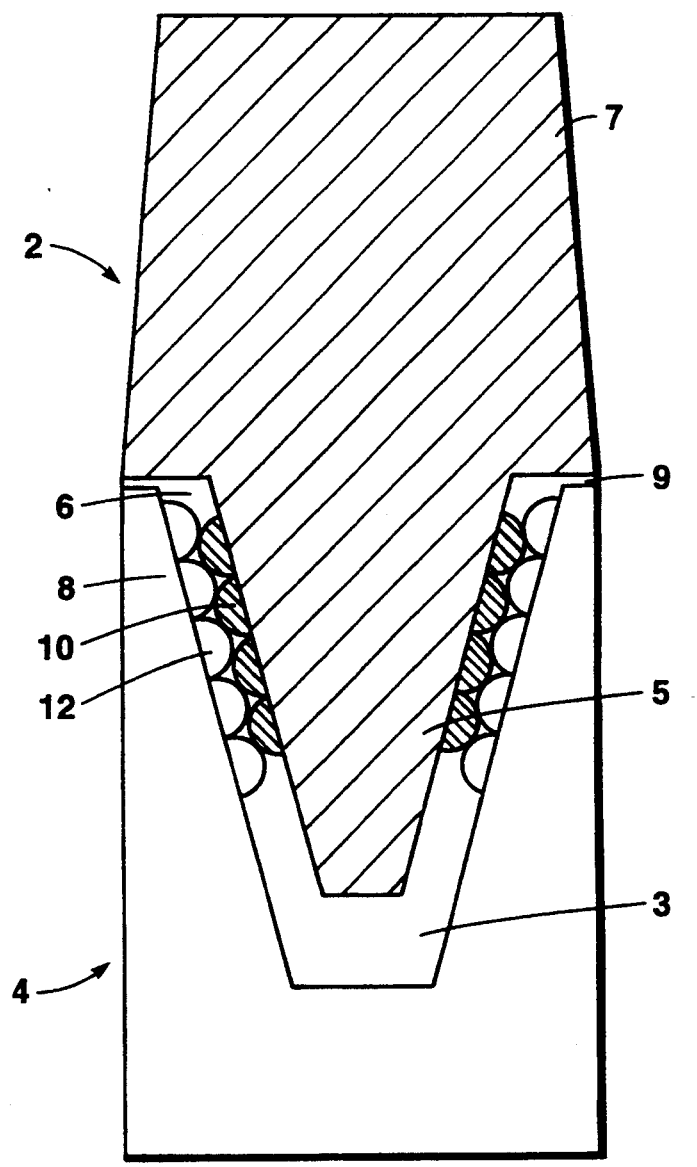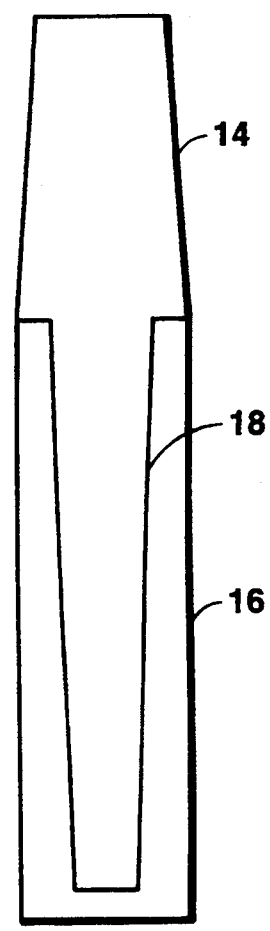
Fig. 1    Fig. 2

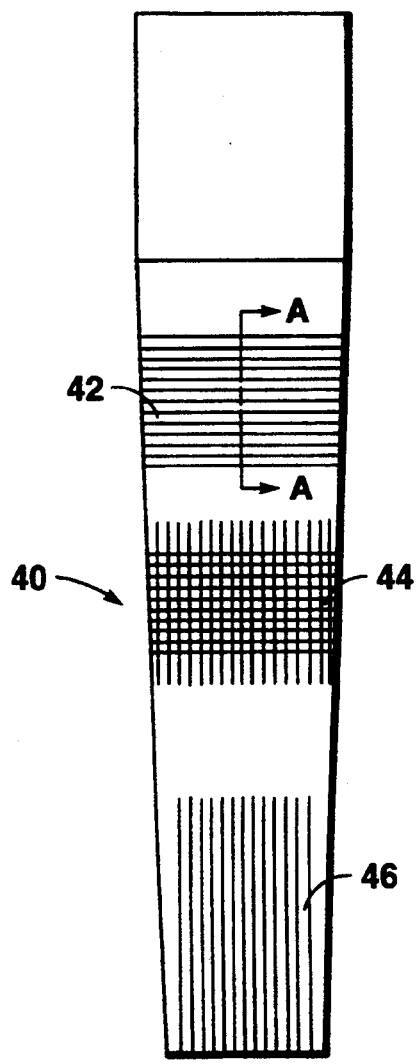
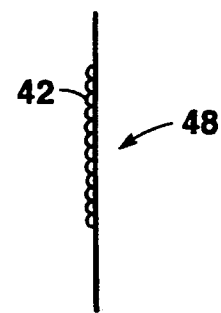
Fig. 5
Fig. 4

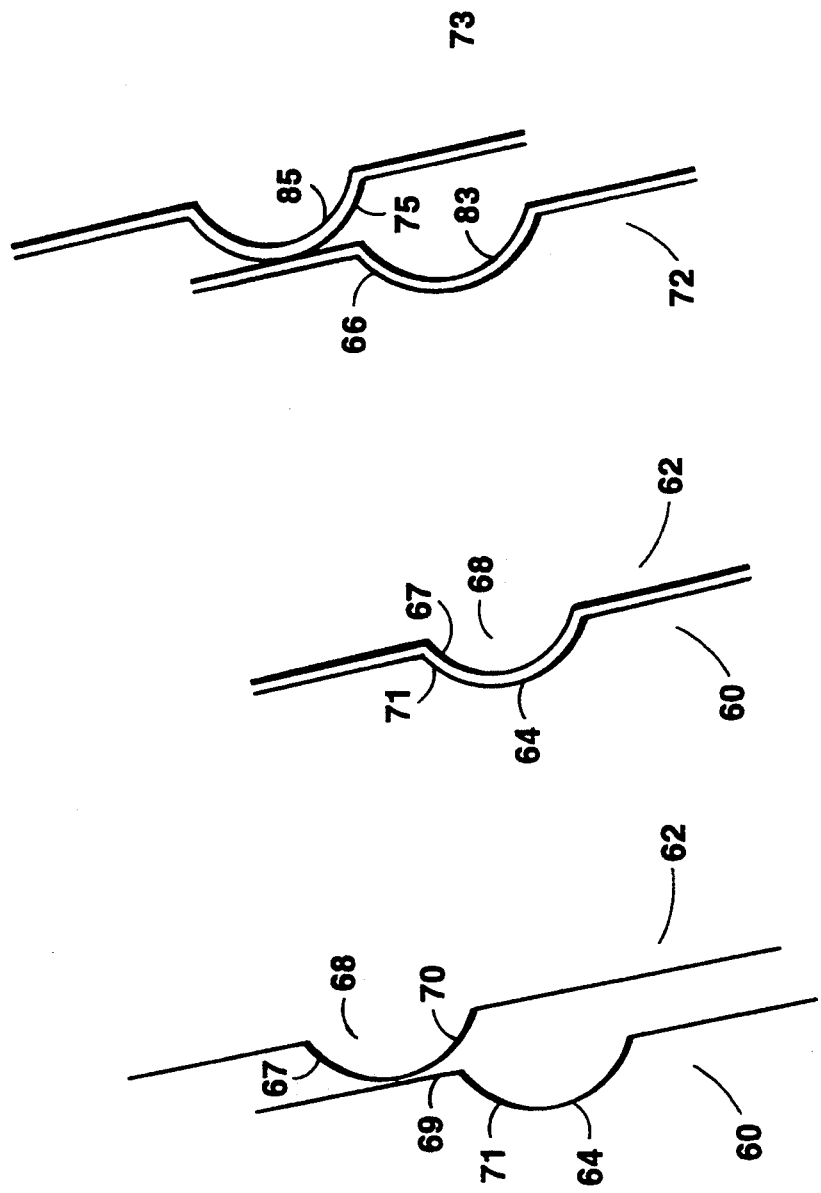

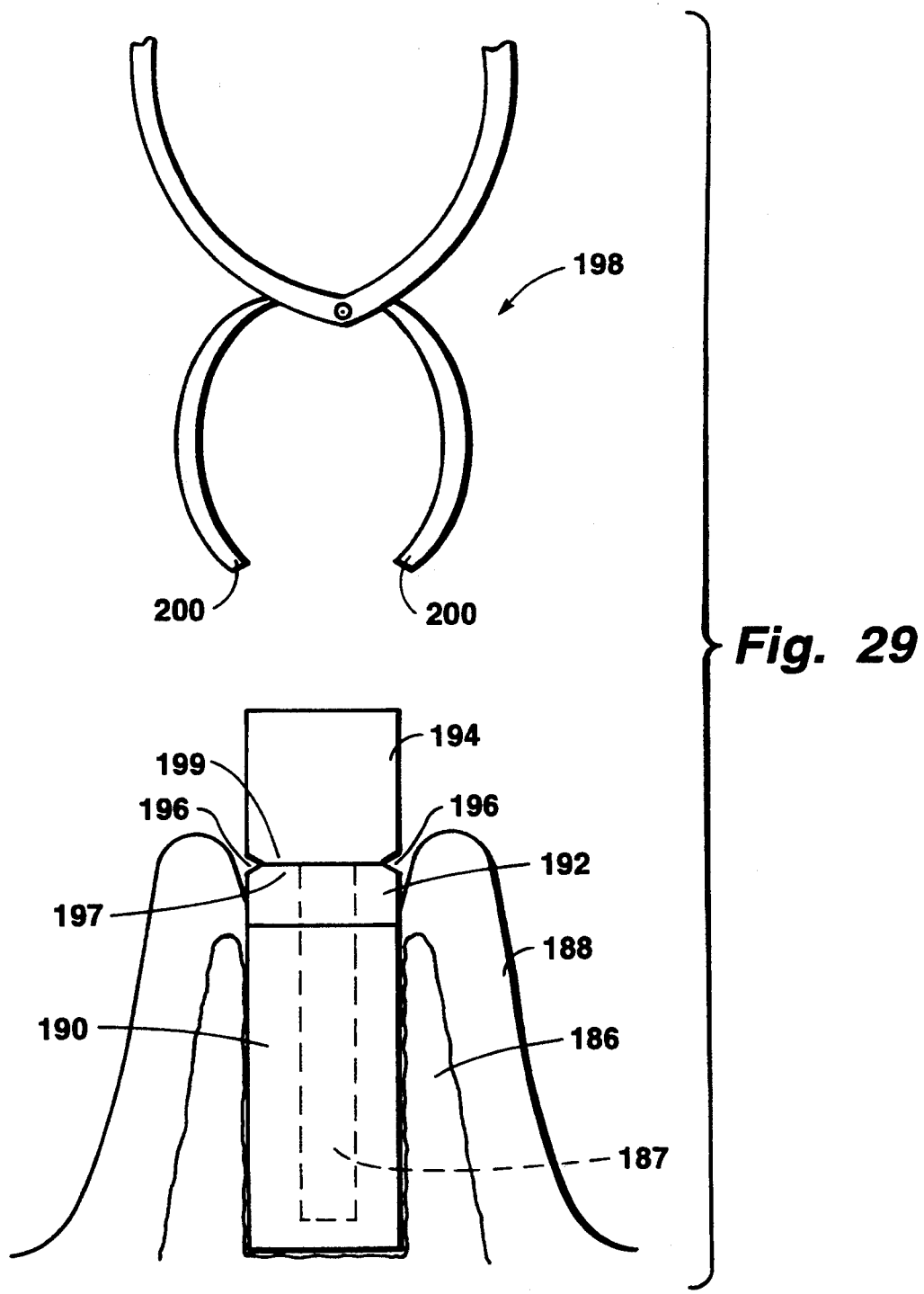

DENTAL IMPLANT POST AND PROSTHESIS CONSTRUCTION

REFERENCE TO RELATED APPLICATION

This application is a continuation-in-part of application Ser. No. 896,602, filed Jun. 10, 1992 now U.S. Pat. No. 5,312,253 which, in turn, is a continuation-in-part of application Ser. No. 814,507, filed Dec. 30, 1991, now U.S. Pat. No. 5,197,881.

BACKGROUND OF THE INVENTION

This invention relates to a dental implant system which can be inserted into the jaw bone of a patient and can be utilized to improve retention of a dental restoration built onto the jaw bone.

Presently, dental implant systems are utilized to fix a synthetic tooth structure to the jaw bone of a patient in order to replace a missing tooth. The implant system includes an implant which is inserted into a hole in the patient's jaw bone drilled by a dentist. The implant includes a hole designed to receive a dental post which, in turn, serves to retain a core upon which a tooth crown is built. After the implant is inserted into the jaw bone, it is covered by the patient's gum and allowed to heal from 3-6 months while the bone grows to surround and retain the implant. The gum then is opened to expose the implant. At this time, impressions are made or a post needed to support the crown is positioned into the implant. At the present time, these posts are screwed into place with the implant having a helical path and the post having a mating helical thread. The post bottom can have threads or can have a hollow core for a screw to unite the post and implant. A screw system alone does not provide an antirotation characteristic to the implant system and can unscrew and loosen.

A problem with this system is that the screws break during implacement and during function. Also, the screws are small and may be dropped in the mouth accidently or they are difficult to place into the back portion of the mouth. In addition, it is difficult to determine if a post is fully seated with a screw system. After the post is positioned in the implant, it extends above the gum so that a dental prosthesis including a core can be retained in place. All single posts must resist normal rotational forces which occur during normal or abnormal functions. In general, preformed posts do not provide good stability against rotational force because they are circular and rotate easily when placed in a circular hole in the implant. Screw type posts can exert large lateral stresses which lead to potential implant fixture fracture and implant loss. If filling material is placed around a preformed post above the jawbone to accept a crown after the post is positioned, the strength and long term stability of this material becomes a weak link in long term success of the crown. In addition, proper design of the post above the jaw line is critical to resist rotation or dislodging of the filling material from the post.

It has been proposed in U.S. Pat. Nos. 4,480,997; 4,490,116 and Re 31,948, to utilize a threaded dental post which is introduced into the bore of a tooth stub by being rotated to thread the post into position. The dental post includes a stem portion having a slot extending through the stem thickness and along its length which renders the stem being formed of two legs each having its outside surface threaded. The outside surface of the legs intimately contact the walls of the bore so that the threads on the legs can engage the walls. In addition, a spring-like connection for the two legs is provided so that a radial outward spring force is applied to the legs to force them against the bore walls. These dental posts are undesirable since a rotational force must be applied to the post to position it properly into the bore. This positioning process is undesirable since it is time consuming and causes the patient discomfort. In addition, the possibility exists that the post will be threaded too far which will result in fracture. Furthermore, the radially outward forces of the legs on the tooth stub can result in fracture of the tooth stub over time. The same problems are present when these posts are used in conjunction with an implant positioned in a jaw bone.

U.S. Pat. No. 1,534,409 discloses a two legged post having corrugated surfaces which fit into a root canal having generally parallel walls. This surface design materially reduces the post surface area which contacts the canal walls and thus post retention relies primarily upon cement adhesive strength.

Accordingly, it would be desirable to provide a dental implant having a bore for a dental post which can be inserted into a hole in the jaw. In addition, it would be desirable to provide a dental implant with means to provide mechanical interaction in order to retain the post in the implant hole while minimizing or eliminating forces on the implant walls exerted by the post and be able to place a post in any rotational position around 360 degrees. Furthermore it would be desirable to provide a post which resists rotational forces. Furthermore, it would be desirable to provide a system for utilizing such a dental implant and post system which facilitates the placement of a core and a crown. Furthermore, it would be desirable to provide such a system for joining the prosthesis to the post.

SUMMARY OF THE INVENTION

This invention provides a dental implant utilized in conjunction with a dental post in order to support a dental prosthesis. The implant is sized to be positioned within a hole of the jaw bone of a patient. The implant has an internal hole or bore to permit positioning of a dental post therein. The wall of the implant bore has a surface which includes extensions shaped as ridges, spheres, squares or other like shapes. The post is made of a matching size to the bore such that placement of the stem of the post into the bore of the implant provides an exact fit. The surface of the post stem includes a matching series of extensions in the form of ridges, spheres, squares, triangles or other like shapes which are in matching relationship with the extensions on the implant bore wall. The interacting surface of the post stem to the surface of the bore of the implant allows placement of the post such that contact of the surface ridges or like structures does not occur until the post is placed part way into the bore of the implant. At initial contact between extensions on the bore wall and on the post stem, the bottom portion of the extensions of the post contact the upper portion of the extensions of the bore of the implant. After this initial contact, elasticity of the material forming the extensions will allow compression such that the extensions of the post will slide over the extensions of the implant. Mating extensions on opposing surfaces of the post and implant or the post and core first contact each other to effect compression of the extensions so that they can move past each other under the influence of the positioning force. After having moved past each other, they are positioned in indentations adjacent to the extensions and one expanded therein. This alternating expansion and contraction is continued until the positioning force ceases so that extension preferentially are positioned in indentations on mating surfaces and the totality of the frictional forces of the extensions in the indentations provides a strong frictional force which positions the post in place with either the implant or core. In one embodiment, the sides of the bore of the implant and the post are parallel to each other and in other embodiments the bore and the post are tapered. The degree of taper varies from 1 degree up to but less than 60 degrees. The preferred taper would be between 2 degrees and 10 degrees. The force required for placement will be determined by the amount of taper, the size of the extensions, the placement of the extensions, the elasticity of the material forming the extensions and the amount of permanent deformation of the material. The post can be placed in any rotational position of 360 degrees which, for example, provides ease of alignment of an angled post into its desired position within the mouth so a tooth constructed on the exposed portion of the post aligns properly with adjacent teeth and opposing teeth.

Chewing forces exerted by the patient are greater in a downward direction, toward the gums, and less in an upward direction away from the gums. An evaluation of the amount of force generated during chewing in these two directions will determine the amount of force which the degree of taper and extensions will be required to prevent dislodgement. The amount of taper, the size and number of extensions, the placement of the extensions, the elasticity of the material forming the extensions and the amount of permanent deformation of the material will be balanced such that sufficient force is achieved to place the post but the forces of chewing will not allow dislodgement. In placement of multiple implants to be joined by a super structure prosthesis, different alignments of posts will prevent dislodgement of posts as the path of withdrawal of one post will block the path of withdrawal of other posts through the prosthesis built on them. If the post is to be fixed and not removed in the future, cement is used to permanently fix the post. Cement is applied independently or precoated on the post stem and activated.

Placement of posts is accomplished by forces of hand pressure or utilization of tools which will apply force such as a hammer or like mechanism. Removal of the post, if desired, can be accomplished by applying sufficient force to cause the elasticity of the extensions to compress past each other. This type of force is accomplished by holding the post and pulling with hand pressure, providing force through a hammering process which provides a means to hang onto the post and a pulling force or through a placement of a notch between the post and the implant which will provide space for placement of a wedge, for example, on a hemostat type instrument. Placement of the wedge into a notch will allow a downward force on the implant and an upward force of the post for removal. Other techniques involve a central hole through a post such that force can be applied to the floor of the implants central bore through the central hole in the post.

A tight seal of the post to the implant is accomplished through beveling, tight tolerances of a butt joint, plastic coating or O-rings. To provide complete customization, as may be necessary in certain circumstances, copings are used which may be ground down or copings which can be cast to after impressions are taken. Further improvements include anti rotation areas such as tabs, slots, oval or out of round bores or flat areas. These areas can also provide a guide for orientation of placement.

This invention provides a means to join a prosthesis to the implant post. A core, crown or prosthesis has an internal hole or bore such that it can be placed over the exposed section of a dental post. The wall of the core, crown or prosthesis bore has a surface which includes extensions shaped as ridges, spheres, squares or other like shapes. The exposed section of a post is made of a matching size such that placement of the core, crown or prosthesis onto the post provides an exact fit. The surface of the post includes a matching series of extensions in the form of ridges, spheres, squares, triangles or other like shapes which are in matching relationship with the extensions on the core bore wall. The interacting surface of the post to the surface of the bore is the same as the interaction of the post stem to the implant bore as described earlier. If the core is to be fixed and not removed in the future, cement is used to permanently fix the core to the post. Cement is applied independently or precoated on the post or core and activated.

BRIEF DESCRIPTION OF THE DRAWINGS

FIG. 1 is an cross sectional view of an implant of this invention.

FIG. 2 is an cross sectional view of an alternative implant of this invention.

FIG. 4 is a cross sectional view of an alternative bottom of a post of this invention.

FIG. 5 is a cross section of the extensions of FIG. 4 through line A—A.

FIG. 11 is a cross sectional view of alternative extensions of the post and implant of this invention.

FIG. 12 is a cross sectional view of the extensions of FIG. 11 in final position.

FIG. 13 is a cross sectional view of alternatives of the post and implant of this invention.

FIG. 15 is a matching post to the implant of FIG. 14.

FIG. 16 is a cross sectioned view of the combined implant of FIG. 14 and the post of FIG. 15.

FIG. 29 is a cross section view of an alternative of this invention in the gums and bone.

DESCRIPTION OF SPECIFIC EMBODIMENTS

Figure 3:
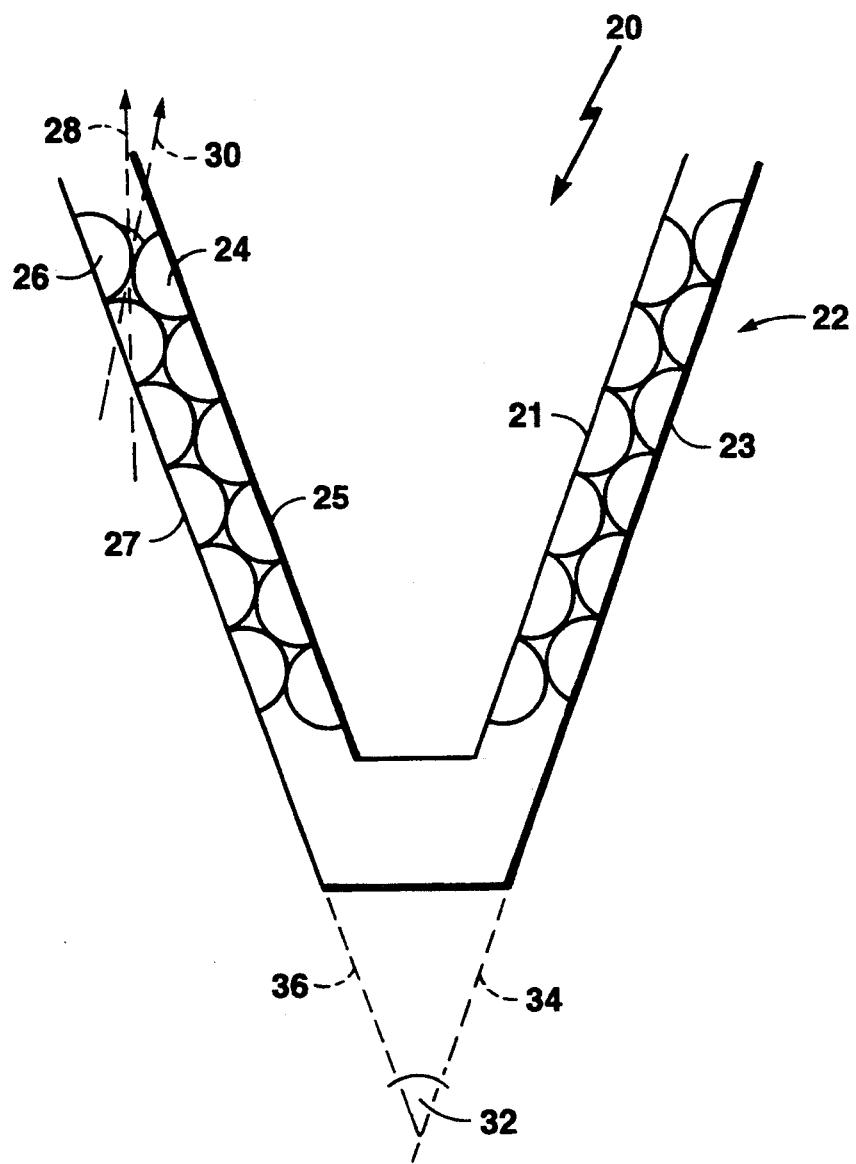
FIG. 3 is a cross sectional view of the interface of the post to the implant bore.

The dental implant of this invention includes a bore having at least one extension which permits locking a mating dental post having at least one extension into the implant without the need for screwing the post to place. The extension of the post or implant is constructed such that the diameter of the post or implant with the extension must compress to engage a slot or extension of the opposing member. An "extension" as used herein is defined as that which extends from the surface of an implant bore or the surface of a dental post or the coping, crown or prosthesis bore. By eliminating the use of a threaded screw, in accordance with this invention, constant pressure on the implant is eliminated, the amount of metal thickness of the post and implant is maximized thereby providing maximum strength. Multiple extensions are used when more retentive force to avoid disengagement is desired. The extensions and slots may vary from a distance of about one micron up to about two millimeters, preferably between one to two hundred microns and 0.1 mm to 0.5 mm. The post, implant and prosthesis are joined and held together by frictional forces between the extensions on post contacting the extensions on the implant and the extensions on the post contacting the extensions on the prosthesis. It is to be understood that these dimensions are exemplary and will vary with the need of the patient. The extensions can be formed by any conventional means such as casting, machining, sand blasting, etching, photo etching coating, oxidizing, laser or other like methods. Materials include a range of plastics, ceramics, biocompatible metals, carbon and graphite by products or like materials and combinations of these materials. The extensions may be of the same material as the post or implant or of a different material such as ceramic, metal, plastic, rubber or other like material. Preferred materials include gold, titanium and/or plastics. Preferred methods of forming extensions include machining, sand blasting or coating.

The degree of taper of the walls of the bore of the implant and the matching portion of the post which fits into the bore of the implant varies from 1 degree from the wall of the bore up to but less than 60 degrees. Preferably the degree of taper is about 1 to 10 degrees from a vertical line within the bore. The force required for placement will be determined by the path of withdrawal of the post, the amount of taper of the internal bore of the implant and matching post, the size and number of the extensions, the placement of the extensions, the elasticity of the material and the amount of permanent deformation of the material after placement.

In still another embodiment, the stem portion of the post does not have the same taper as the walls of the bore of the implant but contact of the extensions is compensated for by varying the size of the extensions.

In still another embodiment, the extensions may be continuous rings around the circumference of the implant bore and post.

In still another embodiment, the extensions may be aligned horizontally and vertically such that the interaction provided retention and anti rotation.

In still another embodiment, multiple dimples and spherical extensions provide specific rotational alignment of the post into the implant in order for placement and therefore engagement to occur.

In still another embodiment, in addition to extensions, the bore of the implant is made out of round such as an oval or clover shape such that the rotational alignment of the post is defined.

In still another embodiment, in addition to extensions, the bore of the implant may be square, rectangular, hexagonal, etc. such that the alignment of the post is defined.

In still another embodiment, in addition to extensions, slots and tabs in the post and implant define alignment and or may provide the retention. Slots and tabs are on the top of the implant, or on the outside of the implant, or in the bore of the implant, or on the floor of the implant bore.

In still another embodiment, in addition to extensions, the slots may be placed in the implant bore and in the post with an independent piece acting as the extension.

In still another embodiment, in addition to extensions, the extensions or slots may occur on the outside or top of the implant and have matching components on the post.

In still another embodiment, an elastic material is provided on the floor of the implant bore or on the bottom of the post. The post extensions are compressed past the implant extensions while compressing the bottom elastic material. Compressive force of the elastic material presses the full seated post upward such that the top of extensions on the post are forced tight to the bottom the extensions of the implant.

In still another embodiment, the stem of the post is provided with legs, a through split and a filling material between the legs. In another alternative the filling material is eliminated.

In still another embodiment, a holder is provided to hold the post during placement.

In still another embodiment, a hammering mechanism is provided to seat the post into the implant.

In still another embodiment, a sliding cylinder or a central hole with a sliding key is provided which allows force to be applied between the post and the implant for removal.

In still another embodiment, a coping is designed to fit over a post implant which is cast onto the implant to form the final desired shape to construct a prosthesis on.

In still another embodiment, a coping is used for customization over an implant/post to construct a prosthesis. There are times when it is necessary to align copings to be parallel to other copings. The proposed copings are of two varieties. First, a coping may be made of a large size which can be hand trimmed to the appropriate smaller dimensions. Secondly, a coping may be made which fits precisely over an implant/post such that metal through a lost wax technique may be cast to it.

To aid in manufacturing tolerances for the fit of parts the post, implant and prosthesis uses tapers or coating of metal with materials such as plastic, or bevels.

Referring to FIGS. 1, the dental implant 4 formed from any suitable dental material includes a central bore 3 and extensions 12. The extensions may be of various sizes or shapes including hexagonal, square, rectangular, circular, oval, combinations or the like or the same size in relation to each other and are positioned at different vertical heights within the bore 3. The bore 3 can have a horizontal cross section of any desired shaped cross-section preferably non circular. A hexagonal shape permits positioning of stem 6 of post 2 in 6 different positions, for example. Of course, larger or smaller number of facets forming the bore shape can be used. The bore also can be circular, elliptical or the like. For convenience, the dental post 2 is shown with eight extensions 12. However, it is to be understood that any plurality of extensions including up to millions can be formed conveniently on a microscopic level on the stem 6. The extensions 10 and extensions 12 or slots are placed on wall 6 of post 2 or wall 8 or implant 4 such as by conventional molding, machined, casting, sand blasting, etching, oxidizing, or like processes. The dental post 2 is inserted into the implant 4 by placing the stem 6 of post 2 into bore 3 of implant 4 until extensions 10 of post 2 contact extensions 12 of implant 4. Force is applied to the top of post 2 such that extensions 10 and extensions 12 compress to slide past each other. Upon sliding past each other, extensions 10 and extensions 12 expand to form their original shape. Extensions 10 engages the underside of extensions 12 such that force would be required pass extensions 10 upward past extensions 12 and therefore to remove post 2.

The dental post can be made of a variety of sizes. For example, a dental post can extend about 3 to 18 mm into the implant and 1 to 7 mm above the jaw bone. A typical dental post diameter can vary between about 1.5 mm and 4 mm. The extensions can extend a length away from a surface of the implant, post or core a distance between about 1 micron and up to 1 millimeters. When over 200 hundred extensions are to be used, the extensions will preferably be between 1 and 200 microns. When between 1 and 25 extensions are to be used, the extensions will preferably be between 0.1 and 0.5 millimeters. It is to be understood that these dimensions are exemplary and will vary with the need of the patient. The sides may be parallel or tapered varying from one degree of taper up to but less than 60 degrees preferably between about 2 to 10 degrees. The outside junction of the bottom of the post 2 to the implant top may be may have a bevel 9 to provide a tight fit and less need for extreme tolerances of the extensions 10 and extensions 12.

As shown in FIG. 2, post 14 fits into implant 16 to form a junction 18 where the extensions are microscopic and therefore can not be seen by the naked eye.

Referring to FIG. 3, the post-implant interface of this system is shown with extension 24 of post 20 and extension 26 of implant 22 in a locked position. Extension 24 and extension 26 are sufficiently compressible so that force can be applied to the top of the post and extension 24 slide past extension 26 during placement.

The retentive force of the system will be determined by the angle of taper of wall 27 of implant 22 and the angle of taper of wall 25 of post 20. The interaction and therefore retentive force of extensions 24 and extensions 26 will be dependant on the angle of wall 25 and wall 21 of post 20 to the wall 23 and wall 27 of implant 22 angles. The degree of taper can be defined by extending the lines of wall 23 and wall 27 to a common point 32. The angle to the vertical 31 of line 34 and line 36 defines how much retention is obtained such that when this angle to the vertical is smaller there will be more retention and when it is larger there will be less retention.

Retention will be further defined by the interaction of the path of withdrawal of the post as indicated by arrow 28 and arrow 30 which indicates the tangent of the contact of circle extension 24 to circle extension 26. As the angle of arrow 28 to arrow 30 approaches zero there will be no retention and as the angle increases there will be more retention.

The retentive force will be further be determined by the size and number of the extensions, the placement of the extensions, the elasticity of the material and the amount of permanent deformation of the material after placement.

As shown in FIGS. 4 and 5, post 40 can be provided with horizontal ridge extensions 42 to provide retention, horizontal and vertical ridge extensions 44 for retention and anti rotation and/or vertical extensions 46 for the purpose of anti rotation. FIG. 5 shows a cross section of the horizontal ridges 42 through line A—A. The shape of the ridges may vary from square, rectangular, circular, oval or combinations or like shapes. The pattern may be regular or irregular.

Figure 6:
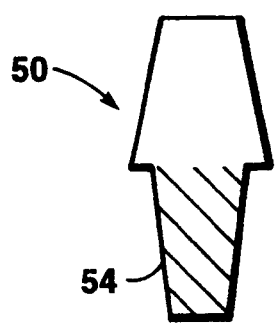
FIG. 6 is an alternative post of this invention.
Figure 7:
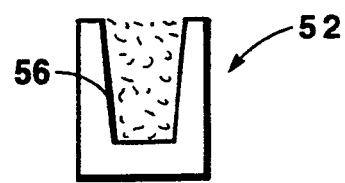
FIG. 7 is a sectioned view of the internal portion of the implant to match the post of FIG. 7.
Figure 8:
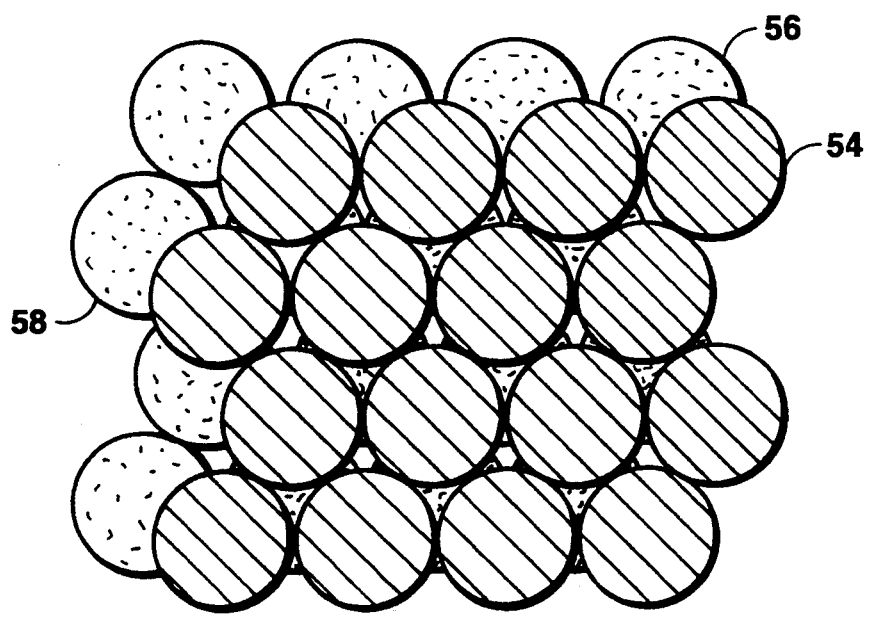
FIG. 8 is an enlargement of the interface of the extensions of the post to the implant.

Referring to FIGS. 6, 7 and 8, post 50 of FIG. 6 has extensions 54 which fit into implant 52 with extensions 56 of FIG. 7. FIG. 8 shows the interaction of extensions 54 between extensions 56. When dimples are used, the extensions on the mating implant or post to the post or implant having dimples will fit into the dimples.

Figure 9:
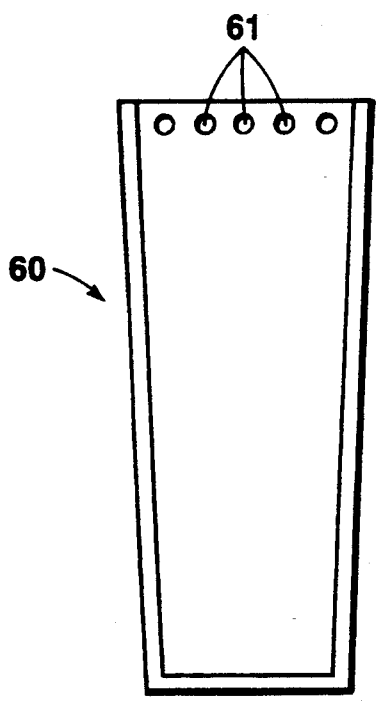
FIG. 9 is a sectioned alternative implant of this invention.
Figure 10:
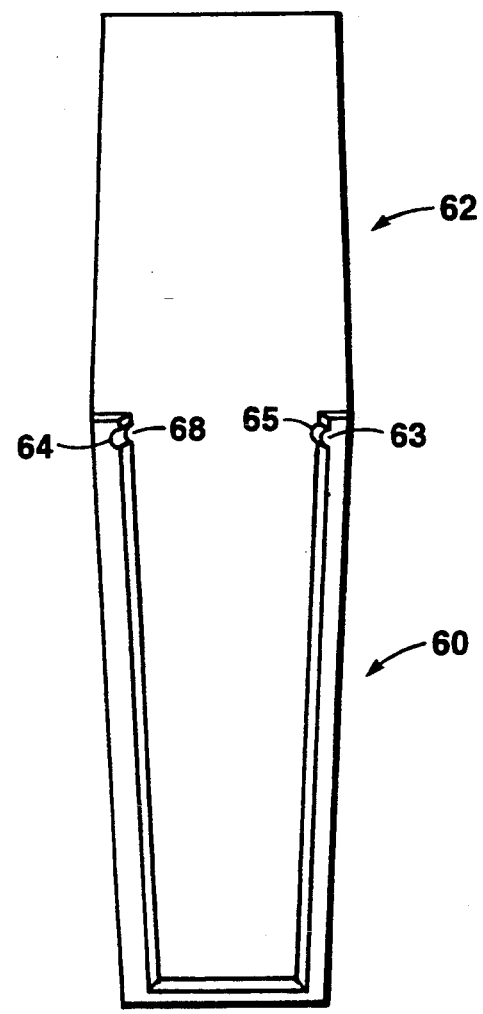
FIG. 10 is a cross sectioned view of a post in the implant of FIG. 9.

Referring to FIGS. 9 and 10, an implant 60 has dimples 64 to accept spherical extensions 68. Single dimples 64 in the same horizontal plane allow reproducible placement in multiple positions a rotational orientation of the post. In an alternative the dimple 70 is placed in the post 62 and the spherical extension 66 is placed in the implant 60. Extension 94 is considered an independent extension because is not permanently attached to post 62 or implant 60.

Referring to FIGS. 11 and 12, implant 60 (not completely drawn) has extension 69 formed by dimple 64. Post 62 (not completely drawn) has extension 68 with lower portion 70 which meets and compresses past extension 69 such that surface 67 of extension 68 meets surface 71 of extension 69 to provide retention. FIG. 13 has implant 72 which has extension 66 which is coated with material 83 and post 73 which extension 85 which is coated with material 75. In an alternative either post 73 or implant 72 are coated. Material 83 and material 75 are the same material or different materials which allow for improved compression of extension 85 past extension 83 such as plastic, rubber or other elastomeric materials, gold, brass, titanium or other metal materials.

Figure 16:
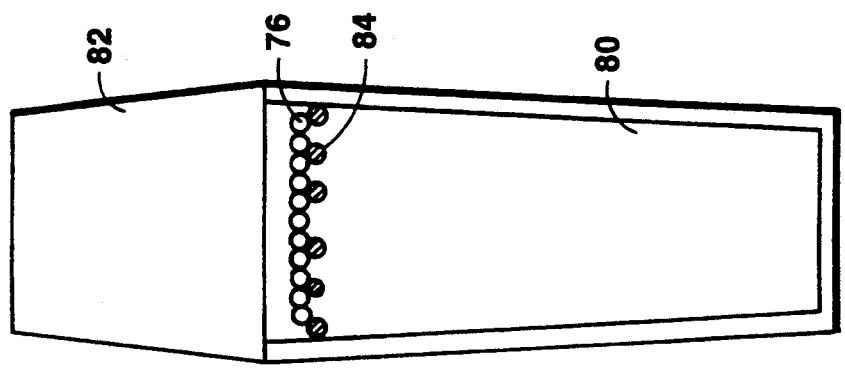
FIG. 16 is a sectioned view of this invention of the post of FIG. 11 in the implant of FIG. 10.
Figure 15:
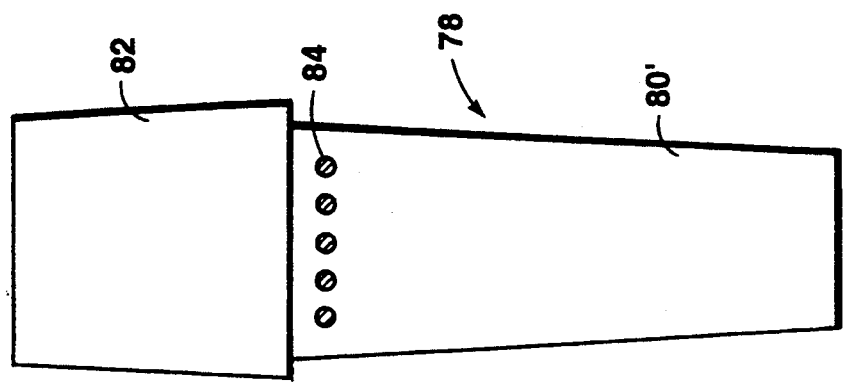
FIG. 15 is an alternative post of this invention.
Figure 14:
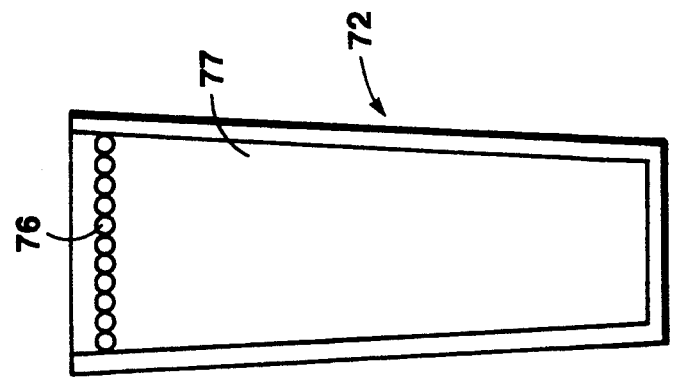
FIG. 14 is a sectioned view of an alternative implant of this invention.

Referring to FIGS. 14, 15 and 16, implant 79 has extensions 76 in central bore 77. Post 78 has stem section 80 which has extensions 84. Upon placement of stem section 80 of post 78 into central bore 77 of implant 78, extensions 84 slide past extensions 76 such that the lower surface of extensions 76 contact the upper surface of extensions 84 and provide retention. One extension 84 contact two of extensions 76 such that anti rotation is achieved.

Figure 17:
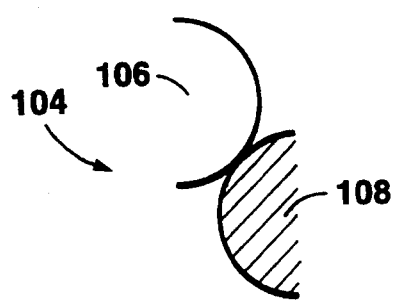
FIG. 17 is a cross section of the interface of the extensions of an alternative post and implant of this invention.
Figure 18:
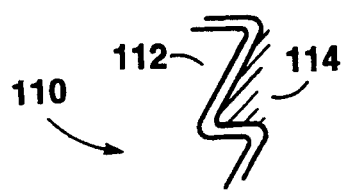
FIG. 18 is a cross section of the interface of the extensions of an alternative post and implant of this invention.
Figure 19:
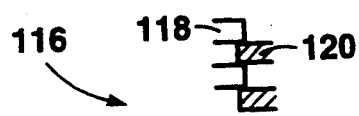
FIG. 19 is a cross section of the interface of the extensions of an alternative post and implant of this invention.

Referring to FIGS. 17, 18 and 19, different shapes of potential extensions are shown. Extension 106 and extension 108 of FIG. 17 show interaction of circular extensions after placement. Extension 112 and extension 114 show the interaction of extensions with combined circular and flat areas. Flat horizontal areas will minimize lateral stress provided by a tapered post when force is applied to the top of the post. Extension 118 and extension 120 show the interaction of primarily flat extensions.

Figure 20:
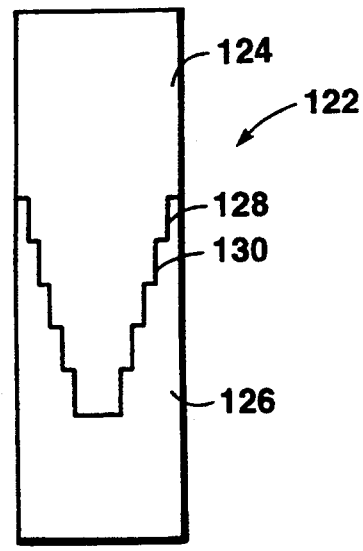
FIG. 20 is a cross section of an alternative post and implant of this invention.

Referring to FIG. 20, shows a possible configuration of post 124 in implant 126. The stepping 128 provides for maximum material and minimum lateral stress on the implant 126 by post 124 to minimize potential implant fracture. The wall 130 of implant 126 and the wall 130 of post 124 are covered with microscopic extensions not seen.

Figure 21:
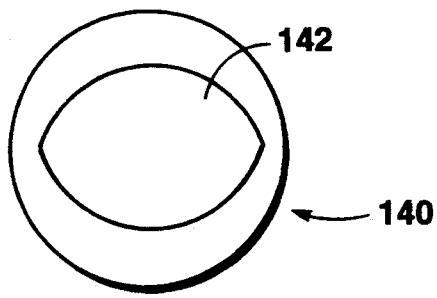
FIG. 21 is a horizontal cross section of the bore of an alternative implant of this invention.
Figure 22:
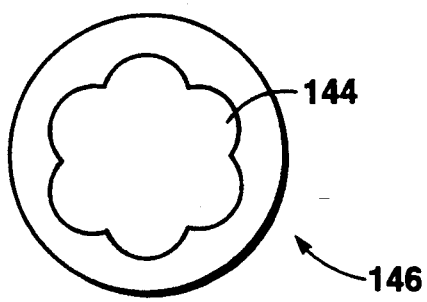
FIG. 22 is a horizontal cross section of the bore of an alternative implant of this invention.
Figure 23:
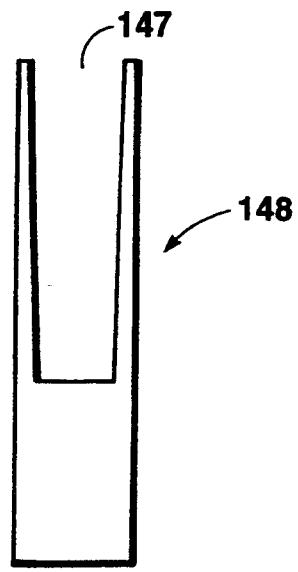
FIG. 23 is a cross section of an alternative implant of this invention.

Referring to FIGS. 21 and 22, a cross section of central bore 142 of FIG. 21 is oval such that only two rotational positions of a post with extensions fitting into an implant with extensions occurs. A cross section of central bore 144 has a clover like appearance such that six potential rotational positions of a post with extensions fits into the implant with extensions. These cross sections prevent post rotation after being inserted into the central bore. A cross section of implant 148 in FIG. 23 shows a tapered central bore 147.

Figure 24:
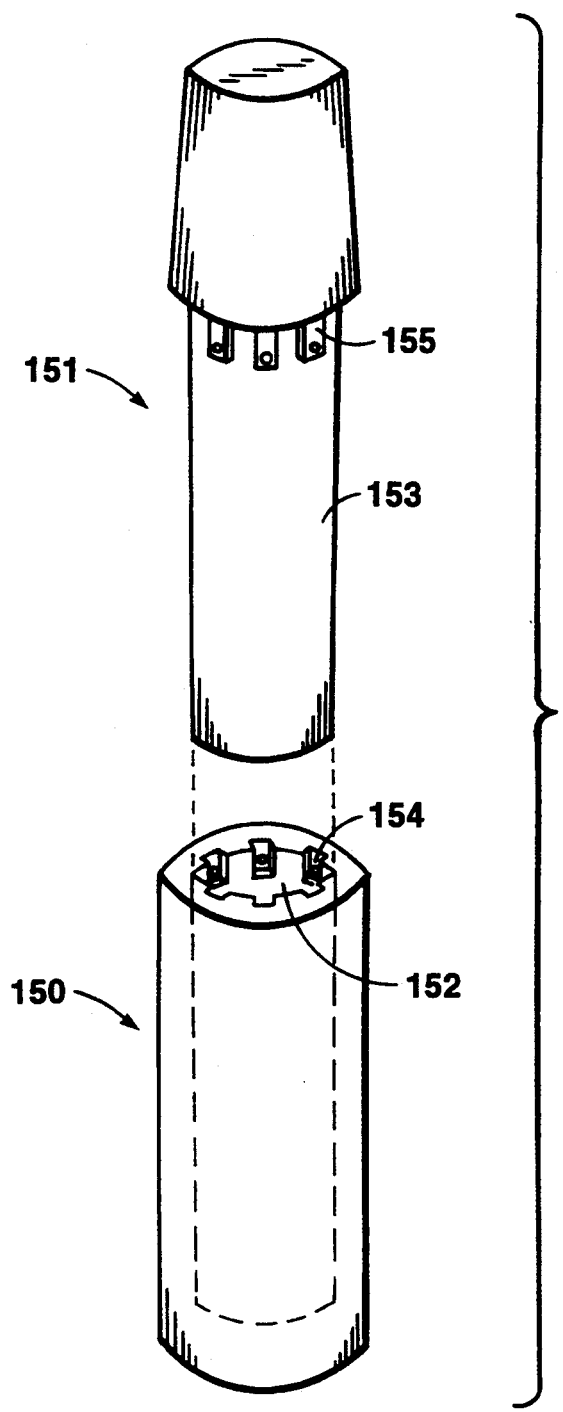
FIG. 24 is the top of an alternative implant of this invention.
Figure 25:
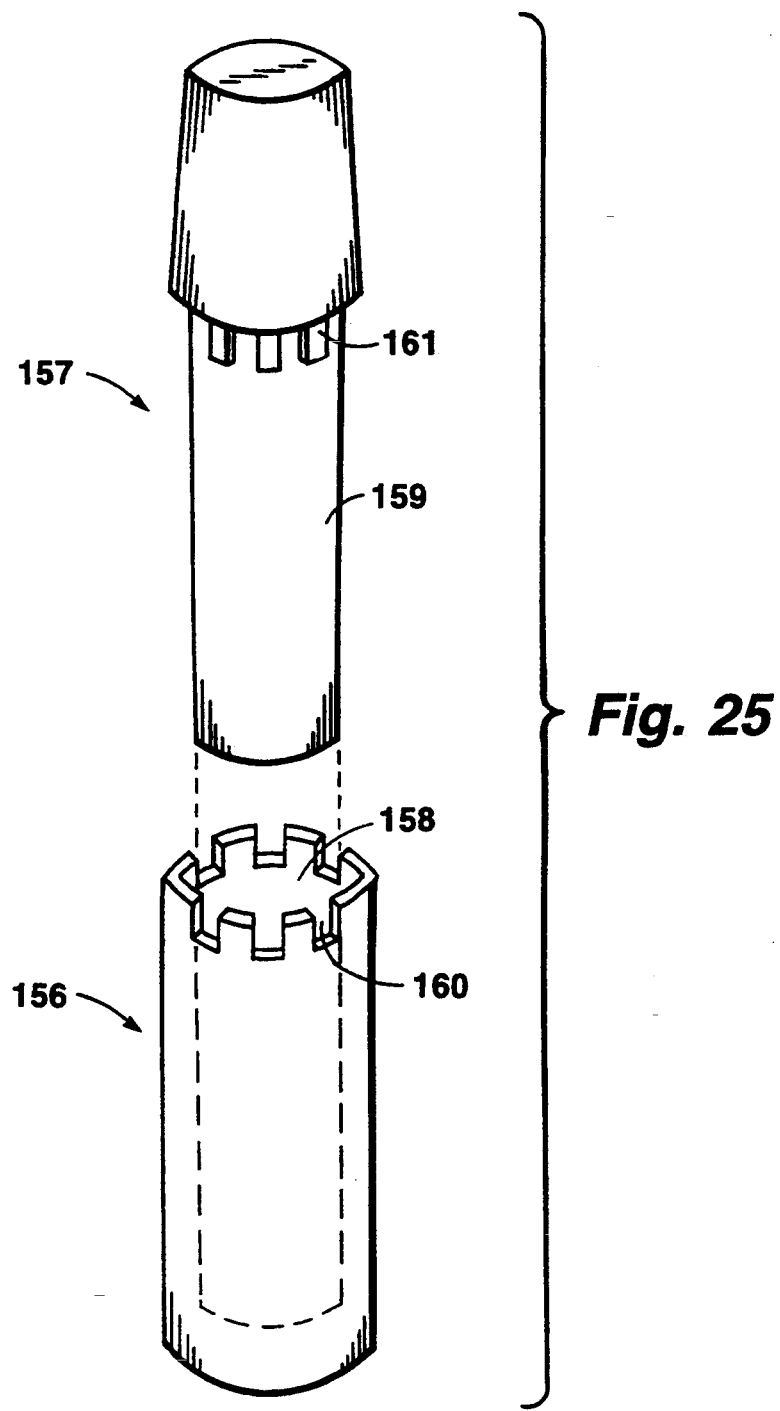
FIG. 25 is the top of an alternative implant of this invention.
Figure 26:
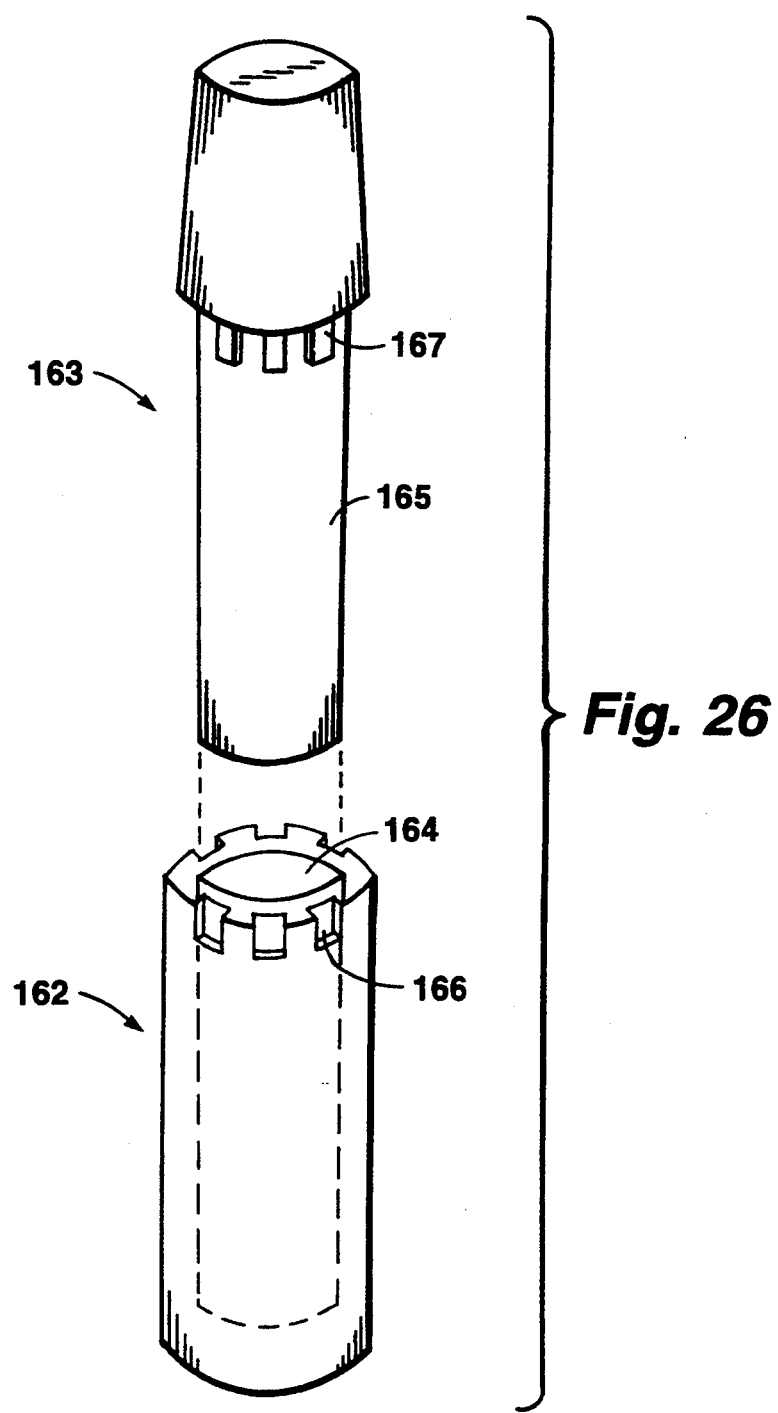
FIG. 26 is the top of an alternative implant of this invention.

Referring to FIGS. 24, 25 and 26, different tab into slot designs are shown. These tab into slot designs prevent rotation of a post in the implant. In addition, these tab to slot relationships can provide retention for the post in the implant. In addition, the tab to slot relationship provides a reproducible rotational position for post placement into the implant. Slot 154 of FIG. 24 is contingent with central bore 152 of implant 150. Extension 155 of post 151 matches slot 154 of implant 150 when post stem 153 is fully seated in central bore 152 of implant 150. The slot 160 of FIG. 25 is through from the central bore 158 to the outside of the implant 156 such that extension 161 of post 157 fits into slot 166 when stem 159 of post 157 is fully seated into central bore 158 of implant 156. The slot 166 of implant 162 of FIG. 26 is open to the outside of implant 162 but not to the central bore 164. Extension 167 of post 163 fits into slot 166 of implant 162 when stem section 165 of post 163 is fully seated in central bore 164 of implant 162. Slots 154, 160 or 166 can be tapered and have extensions to provide retention either with or without other extensions in the bore of the implant, on top of the implant, outside of the implant to provide retention alone. The extension 155, 161 or 167 is used for retention, additional retention or for no retention but dependable resistance to rotational force and reproducible placement. Dimple 165 is an alternative source of retention with a matching extension of a post not shown. It is understood, but not shown that the tabs and slots may be reversed such that the tabs go up from the implant and the slots go into the post.

Figure 27:
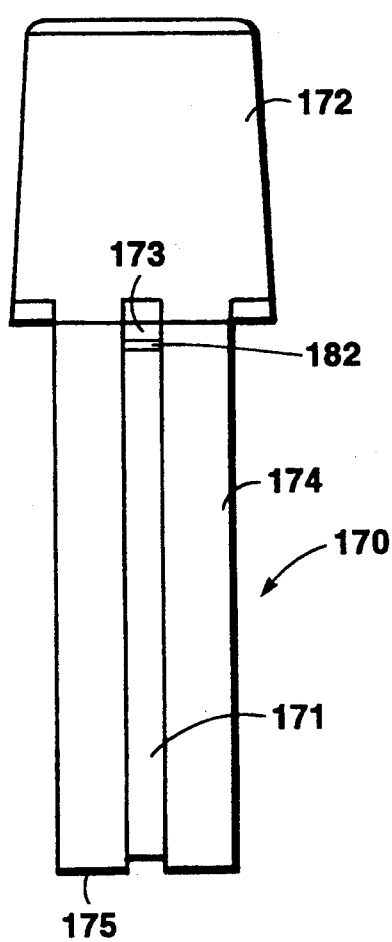
FIG. 27 is a view of an alternative post of this invention.
Figure 28:
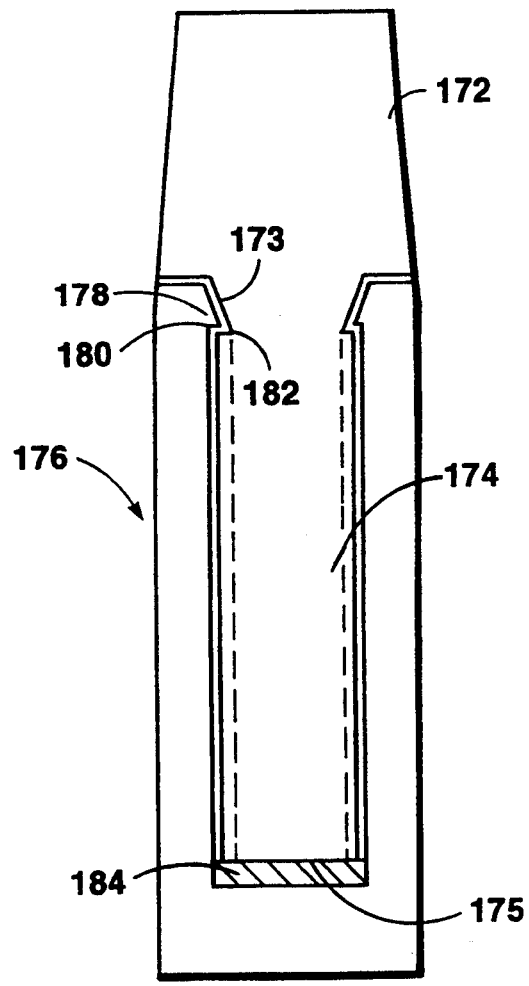
FIG. 28 is a cross section view of the post of FIG. 27 seated in an alternative implant of this invention.

Referring to FIGS. 27 and 28, an alternative post 170 of this invention has slot 171 and retentive slot 173 such that when stem 174 of post 170 is seated in implant 176, extension 178 compresses into slot 173. Simultaneously, elastic material 184 compresses. Upon release of downward force of placement, elastic material 184 forces post 170 upward such that the surface 182 of slot 173 contacts surface 180 of extension 178 to provide a tight fit and prevent movement or accidental dislodgement. This configuration is important when extension 178 must go some distance past slot 173 to disengage the post wall during placement which would necessitate a space between surface 180 and 182. Material 184 will compensate for this space by pushing the post upward and force surface 180 to contact surface 182.

Referring to FIG. 29, a post 194 which has extensions (not shown) is positioned into implant 190 which has extensions (not shown). A technique of removal of post 194 from implant 190 is required. An implant 190 is placed in bone 186 and under gingival tissue 188. Sliding cylinder 192 is placed onto stem 187 of post 194 to bring the top of the cylinder 192 to the general height of the gingival tissue. Various size cylinders may be required for various heights of gingiva. Notches 196 are formed at the interface of the top surface 197 of the cylinder 192 with the bottom surface 199 of post 194. Pliers 198 have wedges 200 which fit into notches 196 such that force may be applied inward to force the post upward and disengage extension which hold the post 194 in implant 190.

Figure 30:
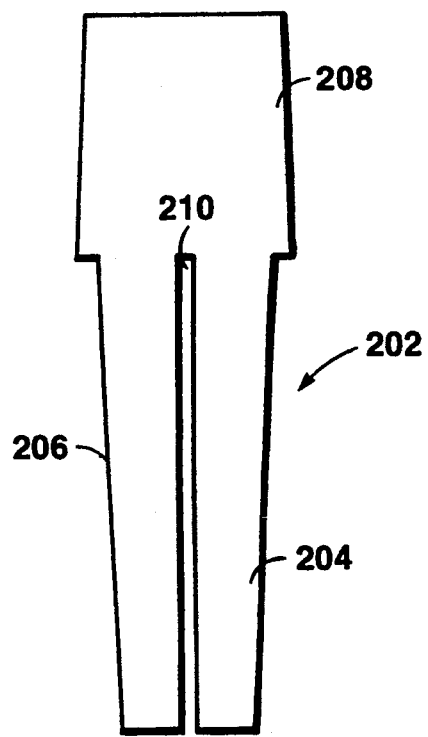
FIG. 30 is a view of an alternative post of this invention.

Referring to FIG. 30, a post 202 having a top section 208 and which has legs 206 and 204 with through split 210. Legs 204 and 206 have extensions 205 which engage extensions or slots on a matching implant (not shown). Legs 204 and 206 form a diameter larger that the diameter of the bore of the matching implant not shown. Compression of the legs 204 and 206 provides maximum contact of the surface of the legs 204 and 206 to the surface of the central bore. Two legs and one split are shown here, however, there are alternatives with two splits, three splits up to as many as sixteen splits and as many as thirty two legs. In an alternative the split 210 is filled with a material such as ceramic, plastic, metal, rubber or like material to provide easier compression of the legs and aid metals which have higher permanent deformation than module of elasticity.

Figure 31:
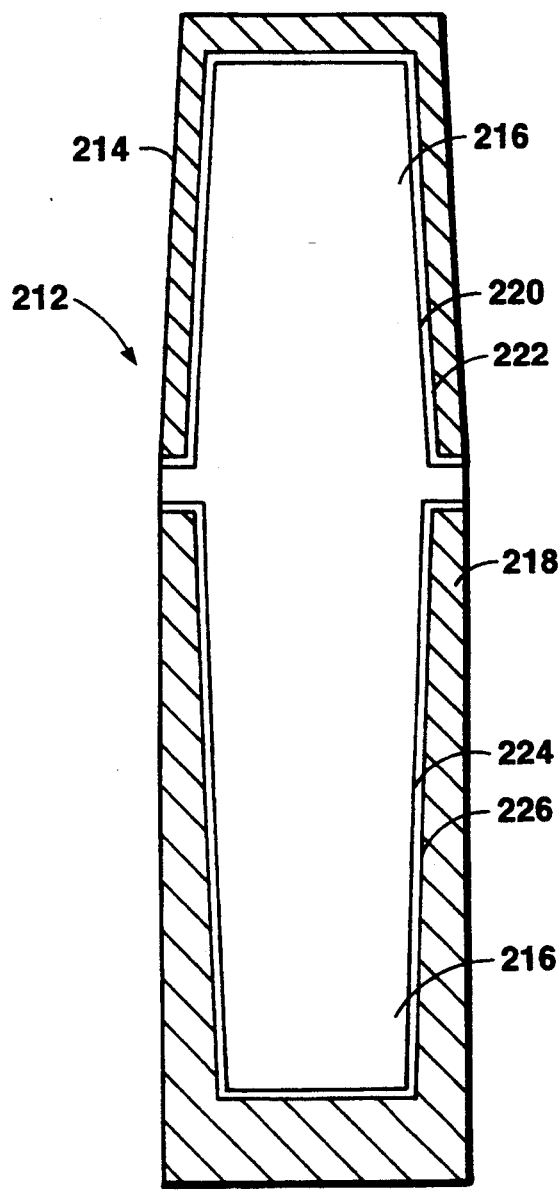
FIG. 31 is a cross section view of an alternative post, implant and core of this invention.
Figure 32:
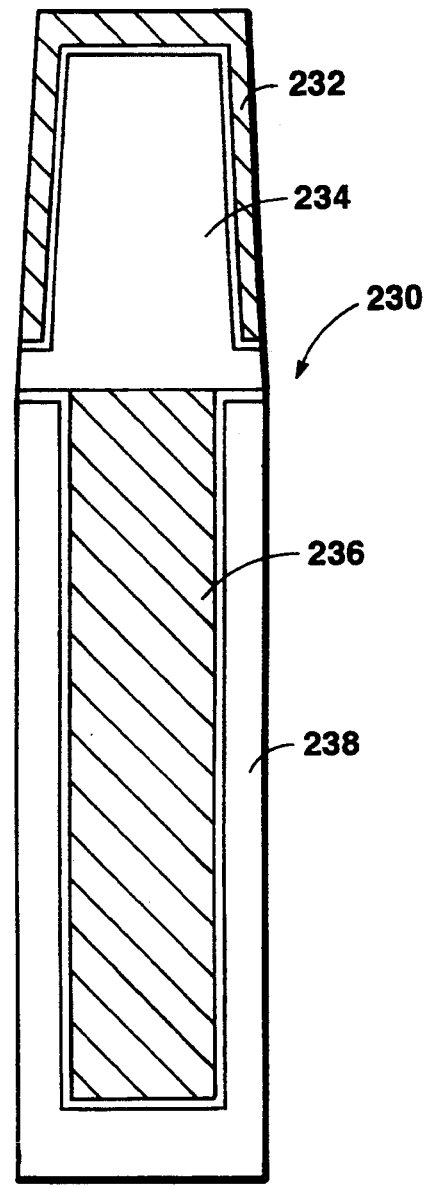
FIG. 32 is a cross section view of an alternative post, implant and core of this invention.

Referring to FIG. 31 and 32, a dental system 230 having a post 216 is placed in implant 218 such that wall 226 of implant 218 has extensions which interact with extensions on wall 224 of post 216. Core 214 has extensions on wall 222 which interact with extensions on wall 220 of post 216. Referring to FIG. 32, post 236 is screwed into implant 238. Core 232 is placed onto the top section 234 of 236 post and maintained in position by extensions on the interacting walls. The core having extensions which cooperate with extensions on the top section of the post can be utilized with any other combination of post and implant or preformed post and tooth stub. That is, the post and implant in this embodiment can be joined together by any other means presently in the art. It is preferred to utilize a dental system wherein extensions are positioned on all of the implant, post and core.

I claim:

1. A dental system for insertion into a bore of a jaw bone of a patient which comprises:
   a dental implant adapted to fit in a bore of said jaw bone, said dental implant having a central bore extending from a top surface of said implant through a portion of the vertical height of said implant,
   at least one first extension extending from and directly attached to a first wall of said central bore,
   a dental post having a stem section shaped to fit into said central bore and having a second wall with at least one second extension attached directly to said post and positioned to frictionally fit with said first extension to retain said dental post within said central bore.

2. The dental system of claim 1 wherein portions of said wall of said central bore are tapered toward each other and portions of said wall of said dental post are tapered toward each other.

3. The dental system of claim 2 wherein a plurality of said first extensions are provided about the entire circumference of said central hole.

4. The dental system of claim 2 wherein a plurality of said second extensions are provided about the entire circumference of said stem.

5. The dental system of any one of claims 2, 3, or 4 wherein the angle of said taper is between about 2 and 10 degrees.

6. The dental system of claim 5 wherein each of said extensions extend a length between about 1 micron and 200 microns.

7. The dental system of claim 5 wherein each of said extensions extend a length between about 0.1 millimeters and 0.5 millimeters.

8. The dental system of any one of claims 2, 3 and 4 wherein the angle of said taper is between about 2 and 10 degrees and
   a core having a second central hole, extending from a bottom surface of said core through a portion of a vertical height of said core,
   at least one third extension extending from and directly attached to a wall of said second hole,
   and at least one fourth extension extending from and directly attached to a top section of a dental post positioned to frictionally fit with said second central hole.

9. The dental system of claim 8 wherein each of said extensions extend a length between about 1 micron and 200 microns.

10. The dental system of claim 8 wherein each of said extensions extend a length between about 0.1 millimeters and 0.5 millimeters.

11. The dental system of claim 1 wherein said hole is formed from parallel walls.

12. The dental system of claim 11 wherein a plurality of said first extensions are provided about the entire circumference of said central hole.

13. The dental system of claim 11 wherein a plurality of said second extensions are provided about the entire circumference of said stem.

14. The dental system of any one of claims 1, 2, 11, 18, 19, 3, 12, 20, 4 or 13 further comprising
   a core having a second central hole, extending from a bottom surface of said core through a portion of a vertical height of said core,
   at least one fourth extension extending from a wall of said second hole,
   and at least one fifth extension on said top section positioned to frictionally fit with said fourth extension to retain said top section within said second central hole.

15. The dental system of claim 14 wherein a plurality of said second extensions are provided about the entire circumference of said second central hole and a plurality of said fifth extensions are provided about the entire circumference of said top section.

16. The dental system of claim 14 wherein each of said extensions extend a length between about 1 micron and 200 microns.

17. The dental system of claim 14 wherein each of said extensions extend a length between about 0.1 millimeters and 0.5 millimeters.

18. The dental system of claim 1 wherein said central bore includes slots having walls with third extensions.

19. The dental system of claim 1 wherein a plurality of said extensions are provided about the entire circumference of said central hole.

20. The dental system of claim 1 wherein a plurality of said second extensions are provided about the entire circumference of said stem.

21. The dental system of claim 1 wherein said stem section has at least one slot extending lengthwise through said stem section to form a plurality of spaced apart legs.

22. The dental system of claim 21 wherein said stem section has one slot.

23. A dental system for placing a core on a top section of a dental post inserted into an implant in the jaw of a patient which comprises:
   a core having a central hole, extending from a bottom surface of said core through a portion of a vertical height of said core,
   at least one first extension extending from and directly attached to a wall of said central hole, portions of said wall being tapered toward each other,
   and at least one second extension extending from and directly attached to said top section positioned to frictionally fit with said first extension to retain said top section within said central hole.

24. The dental system of claim 23 wherein a plurality of said first extensions are provided about the entire circumference of said central hole and a plurality of said second extensions are provided about the entire circumference of said top section.

25. The dental system of any one of claims 1, 2, 11, 18, 19, 3, 12, 20 4, 13, 23 or 24 wherein each of said extensions extend a length between 1 micron and 200 microns.

26. The dental system of any one of claims 1, 2, 11, 18, 19, 3, 12, 20, 4, 13, 23 or 24 wherein each of said extensions extend a length between 0.1 millimeters and 0.5 millimeters.

* * * * *